United States Patent [19]

Semeria et al.

[11] Patent Number: 6,017,426
[45] Date of Patent: Jan. 25, 2000

[54] PROCESS FOR THE PREPARATION OF CERAMIDE-TYPE COMPOUNDS

[75] Inventors: Didier Semeria, Courtry; Michel Philippe, Wissous, both of France

[73] Assignee: L'Oreal, Paris, France

[21] Appl. No.: 09/095,662

[22] Filed: Jun. 11, 1998

[30] Foreign Application Priority Data

Jun. 11, 1997 [FR] France ................................ 97 07240

[51] Int. Cl.[7] .......................... B01D 17/06; C07C 233/00; C07C 229/00
[52] U.S. Cl. ................... 204/157.88; 564/201; 564/215; 564/224; 562/567
[58] Field of Search ....................... 204/157.88; 564/201, 564/215, 224; 562/567

[56] References Cited

PUBLICATIONS

M.P. Vazquez–Tato, "Microwave–Mediated Synthesis of Amides", Apr. 26, 1993, Synlett, vol. 7, p. 506.

B.W. Baldwin et al, "Improved microwave oven synthesis of amides and imides promoted by imidazole; convenient transport agent preparation", 1996, Chem. Commun., vol. 23, pp. 2669–2670.

B. Oussaid et al, "Improved synthesis of oxazoline under microwave irradiation", 1995, Synthetic Communications, vol. 25, No. 5, pp. 659–665.

A.L. Marrero–Terrero et al, "Synthesis of 2–Oxazolines from Carboxylic Acids and alpha, alpha, alpha–Tris(hydroxymethyl) methylamine under Microwaves in Solvent–Free Conditions", Synlett, Mar. 1996, pp. 245–246.

*Primary Examiner*—Edna Wong
*Attorney, Agent, or Firm*—Oblon, Spivak, McClelland, Maier & Neustadt, P.C.

[57] ABSTRACT

A process for the preparation of ceramide-type compounds by reacting, an amino alcohol with a carboxylic acid of defined structures, where the reaction is conducted with irradiation with microwaves and at a temperature of less than or equal to 180° C.

27 Claims, No Drawings

PROCESS FOR THE PREPARATION OF CERAMIDE-TYPE COMPOUNDS

The present application is based on French Patent Application No. 97-07240, filed in the French Patent Office on Jun. 11, 1997, which is incorporated herein by reference in its entirety.

BACKGROUND OF THE INVENTION

1. Field of the Invention

The present invention relates a new process for preparing of ceramide-type compounds.

2. Discussion of the Background

Ceramides, in the natural state, are the principal components of the lipid layers of the epidermis. They are used in the cosmetic field, in the natural or synthetic form, in compositions intended, inter alia, to reduce drying of the skin or to confer better elasticity on it. Alternatively, ceramides are used for the treatment of the hair.

Natural ceramides are generally obtained by extraction from pig skin, bovine brain, eggs, blood cells or plants (see, JP 86-260008 or JP 86-120308).

The disadvantages linked to this type of supply (fragility, contamination, preservation, cost and the like) meant that the chemical synthesis route was soon explored as an alternative to isolation from these natural sources.

Synthetic ceramides were thus already proposed in application EP-A-500 437. These ceramides result from the acylation of the amine functional group of a sphingosine or of a dihydrosphingosine with an activated acid, thus leading to compounds comprising an amide functional group. The acylation reactions can be carried out by numerous methods which are described by J. March in Advanced Organic Chemistry—Fourth Edition—John Wiley & Sons, Inc. p. 417–425 (1992). The activated acid used for the acylation reaction may be, for example, an acid chloride, an ester, an anhydride, an azolide and should be synthesized before carrying out the acylation reaction leading to the formation of the amide functional group of the ceramide. In addition, if the acid, in its nonactivated form, comprises one or more hydroxyl groups other than that of the carboxylic acid group, this or these hydroxyl groups should be necessarily protected so as not to react during the synthesis intended to form the amide bond. This synthesis route therefore requires a prior synthesis step of activating the acid.

It is also known from Mitchell, Reid in J. Am. Chem. Soc., Vol. 53, p. 1879 (1931) that pyrolysis of amine and acid salts can lead to amide bond formation, but this method requires several hours of heating between 160° C. and 220° C. The high temperature necessary for the reaction causes substantial decompositions of the starting materials or of the products formed, thus leading to low yields of synthesized products. Moreover, when amino alcohols are used as starting materials, these pyrolysis reactions predominantly lead to oxazoline-type derivatives instead of the desired ceramides.

The use of microwaves during chemical reactions of amines with acids to produce amides has been described by P. Vazquez-Tato in Synlett, 1993, p. 506. The publication by B. Oussaid, Synthetic Communications, 25(5), p. 659–665 (1995) shows that this type of reaction, carried out with 2-thienylacetic acid and ethanolamine, leads to a mixture of amide and ester, with an amide yield of 40%. A. L. Marrero-Terrero, Synlett, p. 245 (1996) shows that the reaction, carried out with α,α,α-tris(hydroxymethyl)methylamine, does not produce an amide but an oxazoline.

SUMMARY OF THE INVENTION

It is an object of the present invention to provide a new process for the preparation of ceramide-type compounds which does not require the use of an activated acid and leads directly to the desired product with a high yield, and, preferably, with a yield of more than 60%. The aim of the invention is also to provide a process for the preparation of ceramide-type compounds which does not require the protection of the hydroxyl functional groups which may be present in the starting materials.

It has been discovered that the reaction of particular amino alcohols with an acid, with the aid of microwaves, makes it possible to synthesize ceramide-type compounds very rapidly while obtaining good yields and minimizing the formation of by-products, in particular esters and oxazolines.

Accordingly, the objects of the present invention, and others, are accomplished with a process for the preparation of ceramide-type compounds represented by formula (I):

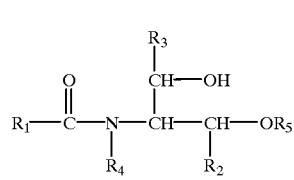

where an amino alcohol of formula (II)

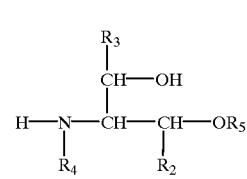

is reacted, in a single step, in the presence of an acid of formula (III) $R_1$—COOH, to form the derivative represented by formula (I), where $R_1$ is
(i) a saturated or unsaturated, linear or branched $C_1$–$C_{50}$, preferably $C_5$–$C_{50}$, and more preferably $C_7$–$C_{30}$, hydrocarbon radical, it being possible for this radical to be substituted with one or more hydroxyl groups optionally esterified with an acid $R_7$COOH, $R_7$ being an optionally mono- or polyhydroxylated, saturated or unsaturated, linear or branched $C_1$–$C_{35}$, preferably $C_{16}$–$C_{30}$, hydrocarbon radical, it being possible for the hydroxyl(s) of the $R_7$ radical to be esterified with an optionally mono- or polyhydroxylated, saturated or unsaturated, linear or branched $C_1$–$C_{35}$ fatty acid,
(ii) a radical R''—(NR—CO)—R', R is a hydrogen atom or a mono- or polyhydroxylated, preferably monohydroxylated, $C_1$–$C_{20}$, preferably $C_1$–$C_{10}$, hydrocarbon radical, R' and R'' are hydrocarbon radicals in which the sum of the carbon atoms is between 9 and 30, R' being a divalent radical, or
(iii) a radical $R_8$—O—CO—$(CH_2)_p$, $R_8$ denoting a $C_1$–$C_{20}$ hydrocarbon radical, p being an integer varying from 1 to 12;

$R_2$ is a hydrogen atom or an optionally mono- or polyhydroxylated, saturated or unsaturated, linear or branched $C_1$–$C_{30}$ hydrocarbon radical, it being possible for the hydroxyl(s) to be etherified with a (glycosyl)$_n$, (galactosyl)$_m$, sulphogalactosyl, phosphorylethylamine or phosphorylethylammonium radical, in which n is an integer varying from 1 to 4 and m is an integer varying from 1 to 8; preferably, $R_2$ is a saturated or unsaturated, linear or branched $C_1$–$C_4$ hydrocarbon radical;

$R_3$ is a saturated or unsaturated $C_1$–$C_{32}$, preferably $C_{10}$–$C_{25}$, hydrocarbon radical, it being possible for this radical to be substituted with one or more hydroxyl groups optionally esterified with an acid $R_7COOH$, $R_7$ being an optionally mono- or polyhydroxylated, saturated or unsaturated, linear or branched $C_1$–$C_{35}$, and preferably $C_{16}$–$C_{30}$, hydrocarbon radical, it being also possible for $R_3$ to be substituted with one or more $C_1$–$C_{14}$ alkyl radicals;

$R_4$ is a hydrogen atom, a methyl radical, an ethyl radical, an optionally hydroxylated, saturated or unsaturated, linear or branched $C_3$–$C_{50}$, preferably $C_{16}$–$C_{27}$, hydrocarbon radical or a radical —$CH_2$—$CHOH$—$CH_2$—$O$—$R_6$ in which $R_6$ is a $C_{10}$–$C_{26}$, hydrocarbon radical or a radical $R_8$—O—CO—$(CH_2)_p$, $R_8$ is a $C_1$–$C_{20}$ hydrocarbon radical, p being an integer varying from 1 to 12; and $R_5$ is a hydrogen atom or a saccharide-type radical, in particular a (glycosyl)$_n$, (galactosyl)$_m$ or sulphogalactosyl radical in which n is an integer varying from 1 to 4 and m is an integer varying from 1 to 8; preferably, $R_5$ is a hydrogen atom;

and the reaction is conducted by irradiation with microwaves at a temperature of less than or equal to 180° C.

Various other objects, features and advantages of the present invention will be more fully appreciated as the same becomes better understood from the following detailed description.

DETAILED DESCRIPTION OF THE INVENTION

The reaction temperature may be at most 180° C. The reaction temperature may also be at least 100° C. The reaction temperature may also be 110° C. to 180° C. Preferably, the reaction temperature is greater than or equal to 100° C. More preferably, the reaction is carried out at a temperature greater than or equal to 100° C., and most preferably between 120° C. and 180° C. These temperatures include all specific values and subranges therebetween, such as 105, 115, 125, 130 135, 140, 145, 150, 155, 160, 165, 170 and 175° C.

Microwaves are understood in the context of the present invention to refer to Ultra-High Frequency waves with frequency ranges from 300 MHz to 30 GHz. It is possible to use more particularly waves whose frequency ranges from 800 MHz to 3000 MHz and preferably from 2400 MHz to 2500 MHz. These frequencies include all specific values and subranges therebetween, such as 400, 500, 600, 700, 900, 1000, 1200, 1500, 2000, 2200, 2300, 2450, 2600, 2800 MHz.

Preferably, in the compounds represented by formula (I) to (III), $R_1$ is a radical as defined according to (i) above, and in particular a hydroxylated or non-hydroxylated, saturated or unsaturated, linear or branched $C_1$–$C_{31}$ alkyl radical; $R_2$ is a hydrogen atom; $R_3$ is a hydroxylated or nonhydroxylated, saturated or unsaturated, linear or branched $C_{10}$–$C_{25}$ alkyl radical; $R_4$ is a hydrogen atom; and $R_5$ is a hydrogen atom.

When the amine of formula (II) and the acid of formula (III) as defined above are mixed, the corresponding ammonium carboxylate is formed initially, generated by the exchange of a proton between these two starting materials. In a variant embodiment of the process according to the invention, it is possible to prepare the ammonium carboxylate beforehand, and then to carry out its irradiation with the aid of microwaves.

The microwave irradiation time during the reaction according to the process of the invention may be very short, that is to say of the order of 5 seconds, or alternatively may be longer, for example up to about 4 hours. Preferably, the reaction mixture may be irradiated for a period ranging from 1 minute to 2 hours. These time periods for microwave irradiation include all specific values and subranges therebetween, such as 30 seconds, 2, 5, 10, 15, 30, 45 minutes, or 1.5, 2.5, 3 or 3.5 hours.

The reaction can be carried out in the presence of solvent, which preferably has a boiling point ranging from 100° C. to 220° C.

Advantageously, the reaction is carried out in the absence of solvent, which avoids a step for removing the solvent once the reaction is complete.

Although the reaction in the presence of microwaves occurs very rapidly, it is possible to accelerate the reaction time by removing the water formed during the reaction. The water formed may be removed either by reducing the pressure of the reaction medium, or by adding a dehydration catalyst to the reaction medium. The pressure of the reaction medium may be reduced to a pressure of less than $10^5$ Pa. As dehydration catalyst, it is possible to use, for example, pyrosulphuric acid, phosphoric acid, para-toluenesulphonic acid, or alternatively, clays, such as montmorillonites.

To carry out the process according to the invention, the amine of formula (II) and the acid of formula (III) are mixed and the mixture is irradiated with the aid of microwaves generated by a microwave oven. The microwave oven power rating may range from 1 W to 2000 W, and more particularly from 1 W to 600 W. These power ratings include all specific values and subranges therebetween, including 2, 5, 10, 25, 50, 100, 200, 300, 400, 500, 700, 800, 1000, 1200, 1500, 1700 and 1900 W.

When the reaction is complete, the products obtained can be isolated from the reaction medium by any process well known to persons skilled in the art.

The yield of the ceramide derivative represented by formula (I) is preferably quite high, such as 60% or higher i.e., at 60%. Preferably, the yield is 60 to 100%, inclusive of all specific values and subranges therebetween, such as 70%, 75%, 80%, 85%, 90%, 95%, 97%, 98%, 99% and 99.5%. The yield may be at least 70% or at least 80%.

Having generally described this invention, a further understanding can be obtained by reference to certain specific examples which are provided herein for purposes of illustration only and are not intended to be limiting unless otherwise specified.

EXAMPLES

Example 1

Preparation of 2-(2'-hydroxyhexadecanoyl) aminooctadecane-1,3-diol 4.9 g (0.018 mol) of 2-hydroxyhexadecanoic acid and 5.4 g (0.018 mol) of 2-aminooctadecane-1,3-diol were mixed in a glass tube; the mixture was irradiated with microwaves with the aid of a Synthewave 402™ apparatus from Prolabo—frequency 2450±50 MHz—modulable power rating 300 W. After an irradiation of 15 minutes at 155° C.±5° C., the reaction mixture was solubilized at high temperature in a mixture of 80 ml of ethyl acetate and 20 ml of heptane. The precipitate obtained was recrystallized from ethanol and 7 g of expected pure product were obtained with a yield of 70%.

Melting point: 88° C.

The $^{13}$C. NMR spectrum is in accordance with the expected structure.

Example 2

Preparation of 2-octadecanoylaminooctadecane-1,3-diol 6.2 g (0.022 mol) of stearic acid and 6 g (0.022 mol) of 2-aminooctadecane-1,3-diol were mixed in a tube and irradiated with the apparatus used in Example 1, under the same frequency and power conditions. After an irradiation of 18 minutes at 140° C.±5° C., the reaction mixture was solubilized in a mixture of 80 ml of ethyl acetate and 40 ml of heptane. The precipitate obtained was recrystallized from ethanol and 8.1 g of expected pure product were obtained with a yield of 72%.

Melting point: 93–101° C.

The $^{13}$C. NMR spectrum is in accordance with the expected structure.

Obviously, numerous modifications and variations of the present invention are possible in light of the above teachings. It is therefore to be understood that within the scope of the appended claims, the invention may be practiced otherwise than as specifically described herein.

We claim:

1. A process for the preparation of a ceramide compound represented by formula (I):

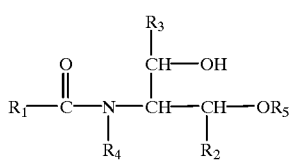
(I)

comprising reacting an amino alcohol represented by formula (II):

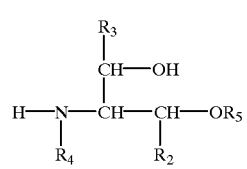
(II)

with an acid represented by formula (III):

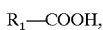

at a temperature of at most 180° C. while irradiating the reaction mixture with microwaves, wherein $R_1$ is
(1) a saturated or unsaturated, linear or branched $C_1$–$C_{50}$ hydrocarbon radical, wherein the hydrocarbon radical is optionally substituted with one or more hydroxyl groups, wherein each hydroxyl group is optionally esterified with an acid represented by the formula $R_7COOH$, wherein $R_7$ is an optionally mono- or polyhydroxylated, saturated or unsaturated, linear or branched $C_1$–$C_{35}$ hydrocarbon radical, wherein each hydroxyl group of the $R_7$ radical is optionally esterified with an optionally mono- or polyhydroxylated, saturated or unsaturated, linear or branched $C_1$–$C_{35}$ fatty acid, (2) a radical represented by the formula R"—(NR—CO)—R', wherein
R is a hydrogen atom or a mono- or polyhydroxylated $C_1$–$C_{20}$ hydrocarbon radical, and
R' and R" are each, independently, a hydrocarbon radical, wherein the sum of the carbon atoms in R' and R" is 9 to 30, and R' is a divalent radical, or (3) a radical represented by the formula $R_8$—O—CO—$(CH_2)_p$, wherein
$R_8$ is a $C_1$–$C_{20}$ hydrocarbon radical, and
p is an integer from 1 to 12;

$R_2$ is a hydrogen atom, or an optionally mono- or polyhydroxylated, saturated or unsaturated, linear or branched $C_1$–$C_{30}$ hydrocarbon radical, wherein each hydroxyl group is optionally etherified with a (glycosyl)$_n$, (galactosyl)$_m$, sulphogalactosyl, phosphorylethylamine or phosphorylethylammonium radical, wherein n is an integer from 1 to 4 and m is an integer from 1 to 8;

$R_3$ is a saturated or unsaturated $C_1$–$C_{32}$ hydrocarbon radical, wherein the hydrocarbon radical is optionally substituted with one or more hydroxyl groups, wherein the hydroxyl groups are optionally esterified with an acid represented by the formula $R_7COOH$, wherein $R_7$ is an optionally mono- or polyhydroxylated, saturated or unsaturated, linear or branched $C_1$–$C_{35}$, hydrocarbon radical, and wherein $R_3$ is optionally substituted with one or more $C_1$–$C_{14}$ alkyl radicals;

$R_4$ is a hydrogen atom, a methyl radical, an ethyl radical, an optionally hydroxylated, saturated or unsaturated, linear or branched $C_3$–$C_{50}$ hydrocarbon radical, or a radical represented by the formula —$CH_2$—CHOH—$CH_2$—O—$R_6$, wherein $R_6$ is a $C_{10}$–$C_{26}$ hydrocarbon radical or a radical represented by the formula $R_8$—O—CO—$(CH_2)_p$, wherein $R_8$ is a $C_1$–$C_{20}$ hydrocarbon radical, and p is an integer from 1 to 12; and $R_5$ is a hydrogen atom or a saccharide radical.

2. The process of claim 1, wherein the reaction is conducted at a temperature of at least 100° C.

3. The process of claim 1, wherein the reaction is conducted at a temperature of 100° C. to 180° C.

4. The process of claim 1, wherein the reaction is conducted at a temperature of 120° C. to 180° C.

5. The process of claim 1, wherein
$R_1$ is a hydroxylated or nonhydroxylated, saturated or unsaturated, linear or branched $C_1$–$C_{31}$ alkyl radical;
$R_2$ is a hydrogen atom;
$R_3$ is a hydroxylated or nonhydroxylated, saturated or unsaturated, linear or branched $C_{10}$–$C_{25}$ alkyl radical;
$R_4$ is a hydrogen atom; and
$R_5$ is a hydrogen atom.

6. The process of claim 1, wherein $R_2$, $R_4$ and $R_5$ are each a hydrogen atom.

7. The process of claim 1, wherein $R_1$ is a $C_1$–$C_{50}$ hydrocarbon radical.

8. The process of claim 1, wherein $R_3$ is a $C_1$–$C_{32}$ hydrocarbon radical.

9. The process of claim 1, wherein
 $R_1$ is a $C_1$–$C_{50}$ hydrocarbon radical;
 $R_3$ is a $C_1$–$C_{32}$ hydrocarbon radical; and
 $R_2$, $R_4$ and $R_5$ are each a hydrogen atom.

10. The process of claim 1, wherein the microwaves have a frequency of 300 MHz to 30 GHz.

11. The process of claim 1, wherein the microwaves have a frequency of 800 MHz to 3000 MHz.

12. The process of claim 1, wherein the microwaves have a frequency of 2400 MHz to 2500 MHz.

13. The process of claim 1, wherein the reaction is conducted in the presence of solvent.

14. The process of claim 13, wherein the solvent has a boiling point from 100° C. to 220° C.

15. The process of claim 1, wherein the reaction is conducted in the absence of solvent.

16. The process of claim 1, wherein the reaction is conducted in the presence of a dehydration catalyst.

17. The process of claim 16, wherein the dehydration catalyst is pyrosulphuric acid, phosphoric acid, para-toluenesulphonic acid, or a clay.

18. The process of claim 17, wherein the clay is a montmorillonite.

19. The process of claim 1, wherein the reaction mixture is irradiated with the microwaves for 5 seconds to 4 hours.

20. The process of claim 1, wherein the yield of the compound represented by formula (I) is at least 60%.

21. The process of claim 1, wherein the yield of the compound represented by formula (I) is at least 70%.

22. The process of claim 1, wherein the yield of the compound represented by formula (I) is at least 80%.

23. The process of claim 1, wherein $R_5$ is a (glycosyl)$_n$, (galactosyl)$_m$ or sulphogalactosyl radical, wherein n is an integer from 1 to 4 and m is an integer from 1 to 8.

24. A process for the preparation of a ceramide compound represented by formula (I):

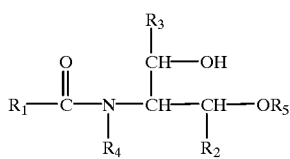

(I)

comprising irradiating an ammonium carboxylate with microwaves at a temperature of at most 180° C., wherein the ammonium carboxylate is obtained by reacting an amino alcohol represented by formula (II):

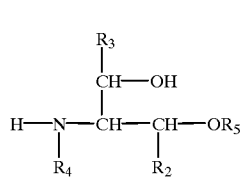

(II)

with an acid represented by the formula $R_1$—COOH;
 $R_1$ is
 (1) a saturated or unsaturated, linear or branched $C_1$–C50 hydrocarbon radical, wherein the hydrocarbon radical is optionally substituted with one or more hydroxyl groups, wherein each hydroxyl group is optionally esterified with an acid represented by the formula $R_7$COOH, wherein $R_7$ is an optionally mono- or polyhydroxylated, saturated or unsaturated, linear or branched $C_1$–$C_{35}$ hydrocarbon radical, wherein each hydroxyl group of the $R_7$ radical is optionally esterified with an optionally mono- or polyhydroxylated, saturated or unsaturated, linear or branched $C_1$–$C_{35}$ fatty acid,
 (2) a radical represented by the formula R″—(NR—CO)—R′, wherein
  R is a hydrogen atom or a mono- or polyhydroxylated $C_1$–$C_{20}$ hydrocarbon radical, and
  R′ and R″ are each, independently, a hydrocarbon radical, wherein the sum of the carbon atoms in R′ and R″ is 9 to 30, and R′ is a divalent radical, or
 (3) a radical represented by the formula $R_8$—O—CO—(CH$_2$)$_p$, wherein
  $R_8$ is a $C_1$–$C_{20}$ hydrocarbon radical, and
  p is an integer from 1 to 12;
$R_2$ is a hydrogen atom, or an optionally mono- or polyhydroxylated, saturated or unsaturated, linear or branched $C_1$–$C_{30}$ hydrocarbon radical, wherein each hydroxyl group is optionally etherified with a (glycosyl)$_n$, (galactosyl)$_m$, sulphogalactosyl, phosphorylethylamine or phosphorylethylammonium radical, wherein n is an integer from 1 to 4 and m is an integer from 1 to 8;
$R_3$ is a saturated or unsaturated $C_1$–$C_{32}$ hydrocarbon radical, wherein the hydrocarbon radical is optionally substituted with one or more hydroxyl groups, wherein the hydroxyl groups are optionally esterified with an acid represented by the formula $R_7$COOH, wherein $R_7$ is an optionally mono- or polyhydroxylated, saturated or unsaturated, linear or branched $C_1$–$C_{35}$ hydrocarbon radical, and wherein $R_3$ is optionally substituted with one or more $C_1$–$C_{14}$ alkyl radicals;
$R_4$ is a hydrogen atom, a methyl radical, an ethyl radical, an optionally hydroxylated, saturated or unsaturated, linear or branched $C_3$–$C_{50}$ hydrocarbon radical, or a radical represented by the formula —CH$_2$—CHOH—CH$_2$—O—$R_6$, wherein $R_6$ is a $C_{10}$–$C_{26}$ hydrocarbon radical or a radical represented by the formula $R_8$—O—CO—(CH$_2$)$_p$, wherein $R_8$ is a $C_1$–$C_{20}$ hydrocarbon radical, and p is an integer from 1 to 12; and
$R_5$ is a hydrogen atom or a saccharide radical.

25. The process of claim 24, wherein
 $R_1$ is a hydroxylated or nonhydroxylated, saturated or unsaturated, linear or branched $C_1$–$C_{31}$ alkyl radical;
 $R_2$ is a hydrogen atom;
 $R_3$ is a hydroxylated or nonhydroxylated, saturated or unsaturated, linear or branched $C_{10}$–$C_{25}$ alkyl radical;
 $R_4$ is a hydrogen atom; and
 $R_5$ is a hydrogen atom.

26. The process of claim 24, wherein
 $R_1$ is a $C_1$–$C_{50}$ hydrocarbon radical;
 $R_3$ is a $C_1$–$C_{32}$ hydrocarbon radical; and
 $R_2$, $R_4$ and $R_5$ are each a hydrogen atom.

27. The process of claim 24, wherein the temperature is at least 100° C.

* * * * *